(12) United States Patent
Yeshurun

(10) Patent No.: US 9,956,182 B2
(45) Date of Patent: May 1, 2018

(54) CANNABIDIOL FOR THE PREVENTION AND TREATMENT OF GRAFT-VERSUS-HOST DISEASE

(71) Applicant: MOR RESEARCH APPLICATIONS LTD., Tel Aviv (IL)

(72) Inventor: Moshe Yeshurun, Elqana (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 0 days. days.

(21) Appl. No.: 14/787,515

(22) PCT Filed: Apr. 29, 2014

(86) PCT No.: PCT/IL2014/050385
§ 371 (c)(1),
(2) Date: Oct. 28, 2015

(87) PCT Pub. No.: WO2014/178048
PCT Pub. Date: Nov. 6, 2014

(65) Prior Publication Data
US 2016/0101063 A1     Apr. 14, 2016

Related U.S. Application Data

(60) Provisional application No. 61/818,525, filed on May 2, 2013.

(51) Int. Cl.
| | | |
|---|---|---|
| A61K 31/05 | (2006.01) | |
| A61K 9/00 | (2006.01) | |
| A61K 38/13 | (2006.01) | |
| A61K 45/06 | (2006.01) | |
| A61K 31/436 | (2006.01) | |
| A61K 31/519 | (2006.01) | |
| A61K 31/573 | (2006.01) | |

(52) U.S. Cl.
CPC ............ *A61K 31/05* (2013.01); *A61K 9/0053* (2013.01); *A61K 31/436* (2013.01); *A61K 31/519* (2013.01); *A61K 31/573* (2013.01); *A61K 38/13* (2013.01); *A61K 45/06* (2013.01)

(58) Field of Classification Search
USPC ........................................................ 514/729
See application file for complete search history.

(56) References Cited

U.S. PATENT DOCUMENTS

| | | |
|---|---|---|
| 6,410,588 B1 | 6/2002 | Feldmann et al. |
| 7,759,526 B2 | 7/2010 | Mechoulam et al. |

FOREIGN PATENT DOCUMENTS

| | | |
|---|---|---|
| WO | 01/95899 A2 | 12/2001 |
| WO | 2008/107879 A1 | 9/2008 |
| WO | 2013/025984 A2 | 2/2013 |

OTHER PUBLICATIONS

Administrator (Medicinal Cannabinoid FAQ: What are THC, CBD, CBN, CBC and . . . ?, Dec. 12, 2011, pp. 1-3).*
Notification Concerning transmittal of International Preliminary Report on Patentability from a counterpart foreign application—PCT/IL2014/050385—2 pages, dated Nov. 12, 2015.
International Preliminary Report on Patentability; and Written Opinion of the International Searching Authority from a counterpart foreign application—PCT/IL2014/050385—1 page, dated Nov. 12, 2015.
Written Opinion of the International Searching Authority from a counterpart foreign application—PCT/IL2014/050385—7 pages, dated Aug. 10, 2014 and dated Nov. 12, 2015.
International Search Report from a counterpart foreign application—PCT/IL2014/050385—5 pages, dated Aug. 10, 2014.
Written Opinion of the International Searching Authority from a counterpart foreign application—PCT/IL2014/050385—7 pages, dated Aug. 10, 2014.
Nagarkatti, Mitzi et al., "Do cannabinoids have a therapeutic role in transplantation?" Trends in pharmacological sciences 31.8 (2010):345-350, published online Jun. 28, 2010; DOI:10.1016/j.tips.2010.05.006; URL:http://www.ncbi.nlm.nih.gov/pmc/articles/PMC2923447//#!.
Pandey, Rupal et al., "Targeting cannabinoid receptors as a novel approach in the treatment of graft-versus-host diesease:evidence from an experimental murine model" Journal of Pharmacology and Experimental Therapeutics 338.3 (2011):819-828, Published online 14.06.2011:DOI:   10.1124//jpet.111.182717;URL:http:www.ncbi.nlm.nih.gov/pmc/articles/PMC3 164345.
Safety and Efficacy of Cannabidiol for Grade I/II Acute Graft Versus Host Disease (GVHD) After Allogeneic Stem Cell Transplantation, URL:http://trialbulletin.com/lib/entry/ct-01596075, May 9, 2012.
Ben-Shabat S. et al. "New Cannabidiol Derivatives: Synthesis, Binding to Cannabinoid Receptor, and Evaluation of Their Antiinflammatory Activity", J. Med. Chem. 2006, 49, 1113-1117 (6 pages).
Raphael Mechoulam et al., "Cannabidiol: an overview of some chemical and pharmacological aspects. Part I: chemical aspects", Chemistry and Physics of Lipids 121 (2002) 35/43 (9 pages).
Dennis B. Leveson-Gower et al., "Mast cells suppress murine GVHD in a mechanism independent of CD4 +CD25+ regulatory T cells", Blood 2013 122(22):3659-3665 (6 pages).
Bertin S. et al., "The ion channel TRPV1 (vanilloid receptor) regulates the activation and proinflammatory properties of CD4+ T cells", Nat Immunol. Nov. 2014; 15(11): 1055-1063. doi:10.1038/ni.3009 (33 pages).
https://www.clinicaltrials.gov/ct2/show/NCT01385124 date: Jun. 28, 2011"Cannabidiol for Graft Versus Host Disease (GVHD) Prophylaxis in Allogeneic Stem Cell Transplantation" (3 pages).
Bhattacharyya S. et al. "Opposite Effects of Δ-9-Tetrahydrocannabinol and Cannabidiol on Human Brain Function and Psychopathology" Neuropsychopharmacology 35:764-774 (2010).
Bisogno T, et al. Molecular targets for cannabidiol and its synthetic analogues: effect on vanilloid VR1 receptors and on the cellular uptake and enzymatic hydrolysis of anandamide. Br J Pharmacol. 134(4):845-52 (2001).
D'Souza D. et al., "Blunted Psychotomimetic and Amnestic Effects of Δ-9-Tetrahydrocannabinol in Frequent Users of Cannabis" Neuropsychopharmacology 33:2505-2516 (2008).

(Continued)

*Primary Examiner* — Kathrien A Cruz
(74) *Attorney, Agent, or Firm* — Browdy and Neimark, PLLC

(57) ABSTRACT

The invention provides methods for preventing, ameliorating and treating the acute and chronic forms of graft-versus-host disease (GVHD) by using Cannabidiol compositions.

12 Claims, No Drawings

(56) References Cited

OTHER PUBLICATIONS

Farrimond et al., "Cannabinol and cannabidiol exert opposing effects on rat feeding patterns" Psychopharmacology, 223(1):117-129 (2012).
Fasinu et al., "Current Status and Prospects for Cannabidiol Preparations as New Therapeutic Agents" Pharmacotherapy 36(7):781-796 (2016).
Guimares et al., "Antianxiety effect of cannabidiol in the elevated plus-maze" Psychopharmacology 100:558-559 (1990).
Lam et al., "Characterization and comparison of recombinant human and rat TRPV1 receptors: effects of exo- and endocannabinoids" British Journal of Anaesthesia, 94(5):649-656 (2005).
Ligresti et al., "Antitumor activity of plant cannabinoids with emphasis on the effect of cannabidiol on human breast carcinoma," Journal of Pharmacology and Experimental Therapeutics, 318(3):1375-87 (2006).
Malfait et al., "The nonpsychoactive cannabis constituent cannabidiol is an oral anti-arthritic therapeutic in murine collagen-induced arthritis" PNAS 97(17):9561-9566 (2000).
Pertwee., "Commentary GPR55: a new member of the cannabinoid receptor clan?" British Journal of Pharmacology, 152(7):984-986 (2007).
Pertwee, The diverse CB1 and CB2 receptor pharmacology of three plant cannabinoids: Δ9-tetrahydrocannabinol, cannabidiol and Δ9-tetrahydrocannabivarin British Journal of Pharmacology, 153(3):199-215 (2008).
Petrocellis et al., Non-THC cannabinoids inhibit prostate carcinoma growth in vitro and in vivo: pro-apoptotic effects and underlying mechanisms British Journal of Pharmacology, 168(91):79-102 (2013).
Ram et al., "Prophylaxis regimens for GVHD: systematic review and meta-analysis" Bone Marrow Transplantation 43, 643-653 (2009).
Shinjyo et al., "The effect of cannabichromene on adult neural stem/progenitor cell" Neurochemistry International, 63(5):432-437 (2013).
Srivastava et al., 9 Tetrahydrocannabinol and cannabidiol alter cytokine production by human immune cells Immunopharmacology 40:179-185 (1998).
Szallasi et al., "Vanilloid (Capsaicin) Receptors and Mechanisms" Pharmacological Reviews 51(2) 159-211 (1999).
Zygmunt, et al. Vanilloid receptors on sensory nerves mediate the vasodilator action of anandamide. Nature, (400):452-7 (1999).
Antin., "Acute graft-versus-host disease: inflammation run amok?" The Journal of Clinical Investigation, 107(12):1497-1498 (2001).
Borrelli et al., "Cannabidiol, a safe and non-psychotropic ingredient of the marijuana plant Cannabis sativa, is Dractive in a murine model of colitis" J Mol Med 87:1111-1121 (2009).
Carrier et al., "Inhibition of an equilibrative nucleoside transporter by cannabidiol: A mechanism of cannabinoid immunosuppression" PNAS 103(20):7895-7900 (2006).
Castro-Malaspina et al., "Unrelated donor marrow transplantation for myelodysplastic syndromes: outcome analysis in 510 transplants facilitated by the National Marrow Donor Program" Blood , 99(6):1943-1951 (2002).
Champlin et al., "Blood stem cells compared with bone marrow as a source of hematopoietic cells for allogeneic transplantation" Blood, 95:3702-3709 (2000).
Choi et al., "Pathogenesis and Management of Graft versus Host Disease" Immunol Allergy Clin North Am 30(1): 75-101 (2010).
Flowers et al., "Comparative analysis of risk factors for acute graft-versus-host disease and for chronic graft-versus-host disease according to National Institutes of Health consensus criteria" Blood, 117(11): 3214-3219 (2011).
Jacobsohn et al., "Acute graft versus host disease" Orphanet Journal of Rare Diseases 2(35):1-9 (2007).
Jagasia et al., "Risk factors for acute GVHD and survival after hematopoietic cell transplantation" Blood, 119(1):296-307 (2012).
Keeble et al., "Involvement of transient receptor potential vanilloid 1 in the vascular and hyperalgesic components of joint inflammation" Arthritis Rheum. Oct;52(10):3248-56 (2005) (Abstract Only).
Kim et al., "Induction of Lethal Graft-versus-Host Disease by Anti-CD137 Monoclonal Antibody in Mice Prone to Chronic Graft-versus-Host Disease," Biol Blood Marrow Transplant 15: 306-314 (2009).
Kozela et al., "Cannabidiol inhibits pathogenic T cells, decreases spinal microglial activation and ameliorates multiple sclerosis-like disease in C57BL/6 mice" British Journal of Pharmacology 163:1507-1519 (2011).
Kozela et al., "Cannabinoids Decrease the Th17 Inflammatory Autoimmune Phenotype" J Neuroimmune Pharmacol 8(5):1265-76 (2013).
Lee et al., "Chronic Graft-versus-Host Disease" Biology of Blood and Marrow Transplantation 9:215-233 (2003).
Lee et al., "A comparative study on cannabidiol-induced apoptosis in murine thymocytes and EL-4 thymoma cells" Int Immunopharmacol. 8(5):732-40 (2008) (Abstract Only).
Szabo et al., "Role of Transient Receptor Potential Vanilloid 1 Receptors in Adjuvant-Induced Chronic Arthritis: In Vivo Study Using Gene-Deficient Mice" The Journal of Pharmacology and Experimental Therapeutics314(1):111-119 (2005).
Liddle, "The Role of Transient Receptor Potential Vanilloid 1 (TRPV1) Channels in Pancreatitis" Biochim Biophys Acta. 1772(8): 869-878 (2007).
McGlave et al., "Unrelated donor marrow transplantation for chronic myelogenous leukemia: 9 years' experience of the gational Marrow Donor Program" Blood. 95:2219-2225 (2000).
McHugh et al., "Inhibition of Human Neutrophil Chemotaxis by Endogenous Cannabinoids and Phytocannabinoids: Evidence for a Site Distinct from CB1 and CB2" Mol Pharmacol 73:441-450 (2008).
Mechoulam et al., "Cannabidiol—Recent Advances" Chemistry & Biodiversity, 4:1678-1692 (2007).
Mielcarek et al., "Prognostic relevance of 'early-onset' graft-versus-host disease following non-myeloablative haematopoietic cell transplantation" British Journal of Haematology, 129:381-391 (2005).
Atakan, "Cannabis, a complex plant: different compounds and different effects on individuals," Ther Adv Psychopharmacol 2:241-254 (2012).
Pavletic et al., "Influence of T-cell depletion on chronic graft-versus-host disease: results of a multicenter randomized trial in unrelated marrow donor transplantation" Blood. 106:3308-3313 (2005).
Rieder et al., "Cannabinoid-induced apoptosis in immune cells as a pathway to immunosuppression" Immunobiology. 215(8): 598-605 (2010).
Sido et al., "Δ9-Tetrahydrocannabinol attenuates allogeneic host-versus-graft response and delays skin graft rejection through activation of cannabinoid receptor 1 and induction of myeloid-derived suppressor cells" Journal of Leukocyte Biology 98(3):435-447 (2015).
Watzl et al, "Influence of marijuana components (THC and CBD) on human mononuclear cell cytokine secretion in vitro," Drugs of Abuse, Immunity, and Immunodeficiency, Edited by Friedman et al, Plenum Press, New York, pp. 63-70 (1991) (also cited as Adv Exp Med Biol 288:63-70 (1991)) (pp. 63-64 Only).
Weiss et al, "Cannabidiol lowers incidence of diabetes in non-obese diabetic mice," Autoimmunity 39:143-151 (2006).

\* cited by examiner

CANNABIDIOL FOR THE PREVENTION AND TREATMENT OF GRAFT-VERSUS-HOST DISEASE

FIELD OF THE INVENTION

The present invention relates to methods and uses of Cannabidiol compositions in the prevention and treatment of the acute and chronic forms of graft-versus-host disease (GVHD).

BACKGROUND OF THE INVENTION

Graft-versus-host disease (GVHD) is a most frequent complication of allogeneic hematopoietic stem cell transplantation (HSCT) and is associated with significant morbidity and mortality. Mortality rates as a direct or indirect consequence of GVHD can reach 50% despite the prophylactic use of immunosuppressive drugs like cyclosporine, tacrolimus, ATG, methotrexate, and mycophenolate mofetil which are administered for prevention of GVHD. Two distinct types of GVHD are clinically recognized, acute and chronic. The acute form of the disease usually develops within the first three months after transplantation. The skin, liver and gastrointestinal tracts are the main targets of acute GVHD. Newly transplanted donor lymphocytes react to the host tissue antigens, resulting in cell damage to a variety of organs. The incidence rate of acute GVHD is estimated at 30-50% among patients receiving transplant from HLA-identical sibling donors, and 50-70% in patients receiving HLA-matched unrelated transplants. Severe acute GVHD (grade III-IV) occurs in up to 20% of recipients of related donors (Champlin, Blood 2000; 95:3702-3709) and up to 35% of unrelated donors (Castro-Malaspina, Blood 2002; 99:1943-1951, McGlave, Blood 2000; 95:2219-2225, Jagasia, Blood 2012; 119:296-307). Non-relapse mortality in patients who develop acute GVHD has been estimated to be in the range of 28% to 92%. Long term survival after grade I acute GVHD is greater than 90%, contrasting with 80%, 30%, and 10% for grades II, III, and IV, respectively. Chronic GVHD occurs in up to 60% of patients receiving HLA-identical sibling marrow grafts and 70% of patients receiving alternative donor marrow grafts who survive beyond day 100. (Lee, BBMT 2003; 9: 215-233). Symptoms of chronic GVHD usually present between 3 months and 2 years after allogeneic transplantation, about two thirds develop within the first 12 months. Manifestations of chronic GVHD may be restricted to single organ or tissue, but typically 2 or 3 organs are involved. The organs most commonly affected are the skin, mouth, and eyes, with more than 50% of patients demonstrating these manifestations. Other disease sites include the liver, lungs, gastrointestinal tract, musculoskeletal system, and female genital organs.

Chronic GVHD can lead to debilitating consequences such as joint contractures, loss of sight, end-stage lung disease, and mortality from infection. The 3 year risk of non-relapse mortality in patients with chronic GVHD ranges from 28% to 48% depending on the extent of GVHD. Mortality rates are increased in patients with extensive disease (more than limited skin or liver involvement), progressive onset (chronic GVHD evolving directly from acute GVHD), thrombocytopenia, and HLA-non-identical donors. The overall survival rate is 42%, but patients with progressive onset of chronic GVHD have a survival rate of 10%.

Altogether, only less than 20% of transplanted patients do not develop either acute or chronic GVHD (Flowers, Blood 2011; 117(11): 3214-3219).

It is well accepted that acute and chronic GVHD are unique different processes. This fact is emphasized by the observations that chronic GVHD can occur without prior acute GVHD, and that interventions that are successful in preventing or treating acute GVHD most commonly fail to decrease chronic GVHD (Pavletic, Blood 2005; 106:3308-3313, Thomas hematopoietic cell transplantation, $4^{th}$ edition, page 1307, Wiley-Blackwell). Most investigators now consider chronic GVHD as a disease of immune dysregulation that involves donor-derived immune cells and host cell populations and tissues. This process is likely initiated by donor-derived T cells and is both alloreactive (directed against the recipient's histocompatibility antigens) and autoreactive (directed against antigens present on both the donor and recipient). The activated immune response then proceeds unchecked by the thymic or peripheral mechanisms of deletion and immunoregulation. Critical donor or recipient tolerance-promoting mechanisms may be absent.

Conventional treatment of chronic GVHD requires prolonged periods of systemic immunosuppressive therapy with potent drugs such as corticosteroids and cyclosporine. Agents such as mycophenolate mofetil, rapamycin (sirolimus), imatinib and rituximab are used in patients with steroid-refractory chronic GVHD. However, these treatments have limited effectiveness, and cause very often severe adverse effects. Only 50% of patients with chronic GVHD are able to discontinue immunosuppressive treatment within 5 years after diagnosis, and 10% require continued treatment beyond 5 years. The remaining 40% die or develop recurrent malignancy before chronic GVHD resolves. 5 year survival rates of patients with high risk chronic GVHD (platelet counts <100,000/microliter or progressive onset from aGVHD) is only 40-50%.

Thus, developing innovative strategies to prevent and treat GVHD is a major unmet need.

The cannabis plant (*Cannabis sativa*) has been in use for medical purposes for thousands of years. Medical Cannabis is nowadays prescribed for prevention of nausea and vomiting associated with cancer chemotherapy, and for the treatment of anorexia associated with AIDS and cancer.

Cannabis plants produce a group of natural chemicals called Cannabinoids, among them $\Delta^9$-tetrahydrocannabinol (THC), Cannabidiol and ajulemic acid. Cannabidiol (CBD) was first isolated by Adams [J. Amer. Chem. Soc., 6: 2194 (1940)] and its structure was elucidated by Mechoulam and Shvo in 1963 (Tetrahedron 19: 2073). The synthesis of cannabidiol in its racemic form and its natural form were reported in J. Amer. Chem. Soc. 87:3273-3275 (1965), and in Helv. Chim. Acta. 50:719-723 (1967). Cannabidiol is the most abundant cannabinoid, contributing up to 40% of Cannabis extracts, having no psychotropic effects, as opposed to THC.

The immune-modulatory and anti-inflammatory properties of Cannabidiol have been shown in animal models of various inflammatory diseases including multiple sclerosis (Kozela, B J P, 2011), diabetes mellitus (Weiss, Autoimmunity 2006), inflammatory bowel disease (Borrelli, J Mol Med 2009) and rheumatoid arthritis (Malfait, PNAS 2000). CBD mediates its anti-inflammatory effects by suppressing T cell proliferation, by shifting the balance from TH1 to Th2 cytokines, inhibiting the pro-inflammatory cytokine release including INFγ, TNFα, IL-1β, IL-6, IL-17 and stimulating the anti-inflammatory cytokine release including IL-4, IL-5, IL-10, IL-13 (Mechoulam, Chem Biodivers 2007, Carrier PNAS 2006, McHugh, Mol Pharmacol 2007, Lee, Int Immunopharmacol 2008, Weis, Autoimmunity 2006, Borrelli, J Mol Med 2009, Kozela, J Neuroimmune Pharmacol 2013, Kozela BJP 2011, Malfait, PNAS 2000).

Unlike Δ9-tetrahydrocannabinol (THC), cannabidiol binds very weakly to CB1 and CB2 receptors [Mechoulam, R. & Hanus, L. *Cannabidiol: an overview of some chemical and pharmacological aspects. Part I: chemical aspects.* Chem Phys Lipids 121:35-43 (2002)].

CBD does not induce psychoactive or cognitive effects and is well tolerated by humans without significant adverse effects [Varga, K., Lake, K., Martin, B. R. & Kunos, G.

CBD has also been shown to be superior to THC, in inhibiting pro-inflammatory IL-I, TNFα and IFNγ release by peripheral blood mononuclear cells. [Watzl, B., Scuderi, P. and Watson, R. R. *Influence of marijuana components (THC and CBD) on human mononuclear cell cytokine secretion in vitro.* Adv Exp Med Biol 288:63-70 (1991);]

U.S. Pat. No. 6,410,588 describes the use of cannabidiol for treating inflammatory diseases such as rheumatoid arthritis, multiple sclerosis and Crohn's Disease, and medicinal preparations containing CBD for use in treating such diseases.

PCT/IL01/00537 describes pharmaceutical compositions comprising cannabidiol derivatives which have analgesic, antianxiety, anticonvulsive, neuroprotective, antipsychotic and anticancer activity.

Although the prior art teaches several potential therapeutic effects and uses of CBD it does not describe or suggest use of CBD or derivatives thereof in treating GVHD.

Therefore, it is an object of the invention to provide Cannabidiol compositions for use in the prevention and treatment of GVHD.

A further object of the invention is the provision of a method of treating and preventing the onset of GVHD by administering a Cannabidiol composition to a patient undergoing transplantation.

A still further object of the invention is the provision of the use of Cannabidiol compositions in the preparation of medicaments for the prevention or treatment of GVHD.

Further purposes and advantages of this invention will appear as the description proceeds.

SUMMARY OF THE INVENTION

According to one aspect the present invention there is provided a method of preventing, ameliorating or treating graft-versus-host disease (GVHD) in a subject in need thereof. The method comprises the step of administering to the subject a therapeutically effective amount of Cannabidiol or any derivative thereof In some embodiments, the subject is a patient undergoing transplantation. According to a specific embodiment, the subject is a patient undergoing allogeneic hematopoietic stem cell transplantation.

In some specific embodiments, the allogeneic hematopoietic stem cells transplanted in the subject are received from a sibling or an unrelated donor, from bone marrow or peripheral blood hematopoietic stem cell grafts. Alternative sources of hematopoietic stem cells grafts are cord blood units, haploidentical peripheral blood or bone marrow stem cells.

According to some embodiments of the invention, Cannabidiol, or any derivative thereof, is administered to a patient before and or after transplantation. In some specific embodiments the method may further comprise the step of administering of at least one additional therapeutic agent. In some embodiments, Cannabidiol, or any derivative thereof, is administered orally in doses of between about 5 mg to about 600 mg each administration once to three times daily.

According to another aspect there is provided a pharmaceutical composition for preventing or treating GVHD comprising Cannabidiol or any derivative thereof, and a pharmaceutically acceptable carrier.

According to yet another aspect there is provided Cannabidiol or any derivative thereof, for use in the prevention and treatment of the GVHD in a subject.

DETAILED DESCRIPTION OF THE INVENTION

The inventors of the present application have surprisingly found that administration of a composition comprising Cannabidiol to transplanted patients showed significant improvement in terms of reduction in incidence and severity of acute and chronic forms of graft-versus-host-disease (GVHD).

According to one aspect, the present invention provides pharmaceutical compositions for preventing and/or treating acute and/or chronic GVHD, as specified herein below, comprising Cannabidiol, or any derivative thereof. The compositions of the invention may optionally further comprise at least one pharmaceutically acceptable carrier, diluent, excipient and/or additive.

Two main categories of GVHD are now recognized. Acute GVHD occurs usually within 100 days after transplant, while chronic GVHD occurs usually beyond 100 days of transplantation.

Acute and chronic GVHD are distinct disorders, involving different immune cell subsets, different cytokine profiles, different host targets, and respond differently to treatment.

The goal of therapy of acute and chronic GVHD is to stop the destructive immunologic process, alleviate symptoms, and prevent disease progression which may lead to irreversible disability or death. Principal components of GVHD therapy include systemic treatment with immunosuppressive drugs or immune modulators integrated with ancillary therapy (non-systemic treatment directed to control the symptoms such as topical corticosteroids, and cyclosporine eye drops) and supportive care (interventions that are directed at control of organ-specific or systemic symptoms such as antibiotics for prevention of infections and physical therapy). The most widely used initial systemic treatment for acute and chronic GVHD relies on prednisone alone or in conjugation with cyclosporine or tacrolimus. However, the current treatments as well as second line available treatments are not sufficient, cause many side-affects and are intolerable in many cases.

*Cannabis sativa*, also termed marijuana, is a plant known for its medical effects, which include easing of nausea and vomiting, anorexia, and weight loss.

The plant produces a variety of Cannabinoids, including Δ$^9$-tetrahydrocannabinol (THC) and Cannabidiol. The term "cannabinoids" refers to a heterogeneous family of molecules usually exhibiting pharmacological properties by interacting with specific receptors. So far, two membrane receptors for cannabinoids, both coupled to G protein and named CB1 and CB2 have been identified. While CB1 receptors are mainly expressed in the central and peripheral nervous system, CB2 receptors have been reported to be more abundantly detected in cells of the immune system.

THC is the main psychoactive Cannabinoid in Cannabis and is used as a treatment for a number of medical conditions. However, its use is strongly limited by the unavoidable psychotropic effects.

Cannabidiol constitutes up to 40% of *Cannabis sativa* extracts, and is recognized as a major non-psychoactive cannabinoid, with a remarkable lack of any cognitive and psychoactive actions. CBD has potent anti-inflammatory and immunosuppressive effects. CBD has been shown to inhibit cancer cell growth and to reduce anxiety and nausea. CBD, also termed 2-[(6R)-3-Methyl-6-prop-1-en-2-yl-1cyclohex-2-envyl]-5pentylbenzene-1,3-diol, has the molecular formula of $C_{21}H_{30}O_2$. The chemical structure of CBD is shown in Formula I:

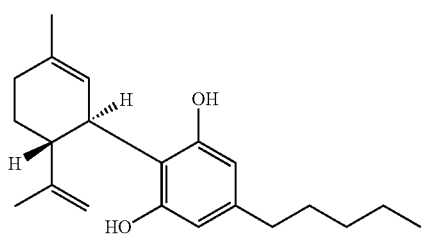

(I)

Cannabidiol is insoluble in water but soluble in organic solvents, such as oil.

The wide range of therapeutic effects can be explained by Cannabidiol's multiple mechanisms of action. Despite its low affinity for CB1 and CB2 receptors, Cannabidiol is capable of antagonizing CB1/CB2 receptor agonists. It has been reported that it can operate as a CB2 receptor inverse agonist and this may in part, contribute to its widely documented anti-inflammatory properties.

Other mechanisms of action include antagonism of the recently discovered GPR55 receptor; type-1 and type 2 vanilloid receptors agonism; 5-HT1A agonism and regulation of intracellular calcium.

The safety of Cannbidiol has been shown in several clinical studies performed in patient suffering from psychological or neurological disorders. The reports indicate that administration of Cannbidiol in doses of up to 1500 mg per day resulted without any significant adverse effects.

The inventors have surprisingly observed a marked alleviation in symptoms associated with both acute and chronic GVHD in transplanted patients who smoked Cannabis in order to control pain and nausea. Interestingly, those patients also reported an increase in the severity of the GVHD symptoms when quitting smoking.

The above observations, together with the anti-inflammatory properties of CBD, as well as the lack of psychotropic effect and low toxicity of the compound, prompted the inventors to examine the therapeutic and prophylactic effects of CBD in chronic GVHD.

The present invention now demonstrates the beneficial effects of treatment with Cannbidiol for the prevention or treatment of acute and chronic GVHD in transplanted patients. More specifically, the present invention demonstrates that treatment with the Cannabidiol compositions of the invention significantly reduces the incidence of acute and chronic GVHD and its severity, as well as other complications associated with the disease such as infections. Accordingly, treatment with the Cannabidiol compositions of the invention prevents the development of GVHD associated symptoms and signs of the various organs and systems, including the skin, nails, mouth, eyes, female genitalia, gastrointestinal tract, liver, lungs, muscles, fascia and joints. The compositions according to the present invention also appear to ameliorate, or resolve acute and chronic GVHD.

Thus, in the first aspect, the invention relates to a method of preventing, treating, ameliorating or curing acute and chronic GVHD. The method of the invention comprises the step of administering to a subject in need thereof a therapeutically effective amount of Cannabidiol or any derivative thereof or any pharmaceutical composition comprising the same.

It should be noted that Cannabidiol or any derivative thereof according to the present invention is a natural product extracted from *Cannabis sativa*, or a synthetic product. Whenever reference is made herein to "*Cannabis sativa*" the same applies also to other Cannabis plants producing Cannabidiol, including *Cannabis indica* and *Cannabis ruderalis*. *Cannabis sativa* is referred to herein specifically, for the sake of brevity.

Cannabidiol, or any derivative thereof according to the present invention, can be administered to patients before or after any type of allogeneic hematopoietic stem cell transplantation, including but not limited to sibling and unrelated-donor bone marrow or peripheral-blood stem cell transplantation, cord blood transplantation, and haploidentical bone marrow or peripheral-blood stem cell transplantation.

Administration of the Cannabidiol compositions to a patient intended to undergo transplantation may start between 14 to 5 days prior to the medical procedure, more specifically 8 days before the transplant. Alternatively, treatment with the Cannabidiol compositions may begin between 1 to 30 days after transplantation, more specifically, 1 day after the transplant.

In some specific embodiments, the method of the invention may optionally further comprise the step of administering at least one additional therapeutic agent, including currently used drugs given to transplanted patients. These additional therapeutic agents, specifically, any immunomodulatory agent or known medicament, may be either combined with Cannabidiol or may be administered separately in an additional separate step having an optional different mode of administration.

In more specific embodiments, the method optionally further comprises the step of administering at least one additional therapeutic agent including but not limited to currently available medicines e.g. cyclosporine, tacrolimus, methotrexate, mycophenolate mofetil, sirolimus, ATG, imatinib or other TKIs, azathioprine, pentostatin, thalidomide, retinoids, anti-CD20, anti-CD52, ECP, corticosteroids and mesenchymal stem cells.

The pharmaceutical compositions containing Cannabidiol according to the present invention can be administered for prophylactic and/or therapeutic treatments. In therapeutic application, compositions are administered to a patient already suffering from acute or chronic GVHD in an amount sufficient to cure or at least partially arrest the condition and its complications. An amount adequate to accomplish this is defined as a "therapeutically effective dose." In prophylactic applications, compositions containing Cannabidiol are administered to a patient who is at risk of developing acute and/or chronic GVHD, i.e. a patient being before or after allogeneic transplantation. Such an amount is defined to be a "prophylactically effective dose". Amounts effective for both prophylactic and therapeutic purposes will depend upon the risk to develop GVHD, the severity of the GVHD condition and the general state of the patient, but generally range from about 0.01 to about 10 mg/Kg body weight, specifically, about 0.5 to about 10 mg/Kg of Cannabidiol per day. Single or multiple administrations on a daily schedule can be carried out with dose levels being selected by the treating physician. It should be noted that doses of Cannabidiol can be elevated every day during the treatment period according to the clinical response of the patient, provided no significant drug related side effects present.

Additionally, the administration of Cannabidiol according to the invention, or pharmaceutical compositions comprising Cannabidiol, may be periodic, for example, the periodic administration may be effected twice daily, three times daily, or at least once daily for 7 days to 180 days, more preferably 90 to 180 days after transplantation for GVHD prevention and 7 days to 12 months (or longer) for the treatment of GVHD.

Specific embodiments of the invention relate to the use of typically two doses per day, each containing at least 10 mg Cannabidiol, but usually not more than a daily dose of 600 mg more preferably each dose containing 300 mg administered twice a day.

In specific embodiments, an exemplary concentration of Cannabidiol in oil, e.g. olive oil, effective for the prevention and/or treatment of GVHD, may range typically between about 1% weight/volume and about 3% weight/volume, more specifically, 2.5% weight/volume.

It should be noted that the Cannabidiol compositions according to the present invention can be prepared in any type of oil, such as canola oil, olive oil, sunflower oil, soybean oil, corn oil, or paraffin oil.

The administration of pharmaceutical compositions comprising Cannabidiol or any derivative thereof according to the invention for the prevention, treatment, amelioration of GVHD in any form, may be any one of oral, sublingual, buccal, rectal, vaginal, parenteral, intravenous, intramuscular, subcutaneous, intra-peritoneal or via oral or nasal inhalation.

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

Pharmaceutical formulations adapted for rectal administration may be presented as suppositories or enemas.

Pharmaceutical formulations adapted for vaginal administration may be presented as pessaries, tampons, creams, gels, pastes, foams or spray formulations.

According to certain embodiments, pharmaceutical compositions comprising Cannabidiol, or any derivative thereof according to the present invention are also useful for parenteral administration, i.e., subcutaneously (s.c.), intramuscularly (i.m.), and intravenously (i.v.). The compositions for parenteral administration commonly comprise a solution of Cannabidiol dissolved in an acceptable carrier.

In one embodiment, the compositions of the invention are particularly suitable for oral administration. The Cannabidiol compositions can be administered from one or more times per day to one or more times per week, including once every other day. Dosing is dependent on the severity of the symptoms and on the responsiveness of the subject to the treatment. The skilled artisan will appreciate that certain factors may influence the dosage and timing required to effectively treat a subject, including but not limited to the severity of the disease, previous treatments, the general health and/or age of the subject, and other diseases present.

The present invention relates to the treatment of subjects, or patients, in need thereof. By "patient" or "subject in need" it is meant any mammal for which administration of the composition of the invention is desired, in order to prevent, overcome or slow down a medical condition.

The terms "treatment", "prevention" and "prophylaxis" refer to the complete range of therapeutically positive effects of administrating to a subject including inhibition, reduction of, alleviation of, and relief from, GVHD, specifically, acute and chronic GVHD. More specifically, treatment or prevention includes the prevention or postponement of development of the disease, prevention or postponement of development of symptoms and/or a reduction in the severity of such symptoms that will or are expected to develop. These further include ameliorating existing symptoms, preventing additional symptoms and ameliorating or preventing the underlying causes of symptoms.

It should be noted that particularly in case of human subjects, administration of the compositions of the invention to the patient includes both self-administration and administration to the patient by another person.

To provide a "preventive treatment" or "prophylactic treatment" is acting in a protective manner, to defend against or prevent something, especially a condition or disease.

As used herein, "disease", "disorder", "condition" and the like, as they relate to a subject's health, are used interchangeably and have meanings ascribed to each and all of such terms.

The term "pharmaceutical composition" refers to an active compound in any form suitable for effective administration to a subject, e.g., a mixture of the compound and at least one pharmaceutically acceptable carrier.

The term "therapeutically effective amount" is intended to mean that amount of a drug or pharmaceutical agent that will elicit the biological or medical response of a tissue or human that is being sought by a researcher, medical doctor, or other clinician, or by the subject himself.

As used herein, a "pharmaceutically acceptable carrier" means a carrier or diluent that does not cause significant irritation to a subject and does not abrogate the biological activity and properties of the administered compound.

A "pharmaceutically acceptable excipient" means an inert substance added to a pharmaceutical composition to further facilitate administration of the compound. Examples, without limitation, of excipients include calcium carbonate, calcium phosphate, various sugars and types of starch, cellulose derivatives, gelatin, vegetable oils and polyethylene glycols.

The following examples, which further describe the invention, are offered by way of illustration and are not intended to limit the invention in any manner.

EXAMPLES

Example 1

Prevention of Acute and Chronic GVHD in Allogeneic Stem Cell Transplanted Patients Forty six (46) patients over 18 years of age undergoing allogeneic hematopoietic stem cell transplantation at the Rabin Medical Center in Israel were recruited. Patients having history of psychosis or asthma, or consuming Cannabis during the last two months before transplantation were excluded from the study.

All patients received standard GVHD prophylaxis consisting of cyclosporine twice a day starting on day −1 with target trough levels ≥200 ng/mL in combination with short course of methotrexate (15 mg/sqm on day +1 and 10 mg/sqm on days +3 and +6). Most patients transplanted from unrelated donors received anti-T-cell globulin (ATG Fresenius) at a low dose of 5 mg/kg on days −3 to −1.

The investigational agent, CBD (STI Pharmaceuticals, Brentwood, Essex, UK) was dissolved in olive oil at a concentration of 2.5% and was orally administered from day −7 through day +30. The starting dose of CBD was 10 mg twice a day, and doses were doubled every other day to a maximal dose of 150 mg twice a day.

To estimate the prophylactic and therapeutic effect of Cannabidiol, the patients were carefully monitored and documented for the presentation of acute and chronic GVHD symptoms, the time of onset, the severity of the symptoms, the responsiveness to treatment, and the occurrence of infections.

Furthermore, we sequentially monitored a panel of 4 serum cytokines (soluble TNF receptor 1 (sTNFRI), soluble IL-2 receptor alpha (sIL2R-alpha), hepatocyte growth factor (HGF), and IL8)). Blood samples were taken at days −7(A), 0(B), +14(C), and +28(D). We assessed the difference in blood levels between the various time points (B-A, C-B and D-C).

Primary end points were safety and cumulative incidence of grade 2-4 and grade 3-4 GVHD by day +100. The secondary end points were cumulative incidence of chronic and severe chronic GVHD, non-relapse mortality (NRM), relapse incidence (RI), and overall survival (OS). NRM mortality was defined as death while the patient was in CR. Cumulative incidence curves were used for acute GVHD and chronic GVHD estimation, taking into account relapse and death as competing risks. Cumulative incidence curves were used for RI and NRM taking into account disease recurrence and death as competing events. Probabilities of OS and LFS were calculated using the Kaplan-Meier estimates.

Median age was 56 (range, 22 to 73) years. Most patients (n=38, 79%) had acute leukemia and 13 patients (27%) had chemo-refractory disease at transplantation. Twenty patients (42%) received allografts from unrelated donors. Thirty five patients (73%) received myeloablative conditioning. Median follow-up of survivors was 10 (range, 1.3 to 18) months. Drug compliance was good, with 32 patients (70%) taking 100% of the doses. Non compliance with study medication was mainly due to mucositis and nausea. Median dose dense among non-compliant patients was 86% (range, 43%-96%). No grade 3 to 4 toxicities related to CBD were observed.

Six patients developed grade 2 to 4 acute GVHD. Two patients had a gut-only involvement, 3 patients had involvement of skin and gut, and 1 patient had involvement of gut and liver. Median time to onset of grade 2 to 4 acute GVHD was 60 days (range, 41 to 150 days). Cumulative incidence rates of grade 2 to 4 acute GVHD at day 100 was 12.4%. Cumulative incidence rates of grade 3 to 4 acute GVHD at day 100 was 5%.

Among patients surviving more than 100 days after HCT (n=33), chronic GVHD occurred in 11 patients (overlap, n=3 and classic, n=8), with a median time to onset of 159 (range, 125 to 335) days. Of the 11 patients, 8 had limited chronic GVHD with a low stage involvement of the oral mucosa and a mild elevation of liver enzymes. In the 3 patients with severe chronic GVHD, organ involvement included eyes (n=3), mouth (n=3), skin (n=3), lungs (n=2) and musculoskeletal (n=1). Cumulative incidence rates of overall and extensive chronic GVHD at 1 year were 43% and 19%, respectively.

Cumulative incidences of relapse at 100 days, 6 months and 12 months after HCT were 12%, 22%, and 31%, respectively. Non-relapse mortality at 100 days, 6 months and 12 months after HCT were 8.1%, 11.6%, and 11.6%, respectively. Overall survival rates at 100 days, 6 months and 12 months after HCT were 84%, 76% and 70%, respectively.

Interestingly, patients with increased D-C serum levels of IL8 and sIL2R-alpha had a relative risk of 3.8 (95% CI 0.8-17.1, p=0.1) and 2.8 (95% CI 1.1-7.5, p=0.05), respectively, for developing chronic GVHD.

The results obtained clearly indicate that administration of Cannabidiol reduces the incidence and severity of acute and chronic GVHD after allogeneic stem cell transplantation. The findings presented herein demonstrate the advantages concurrent with low toxicity and lack of psychotropic effects of Cannabidiol in preventing acute and chronic GVHD.

Example 2

Twelve patients over 18 years of age with extensive chronic GVHD after allogeneic HCT were recruited at the Rabin Medical Center in Israel. Patients having a history of psychosis or asthma, or consuming Cannabis during the last two months before transplantation were excluded from the study.

Patients were presently treated with a calcineurin inhibitor (cyclosporine or tacrolimus) with or without oral prednisone.

Patients were given oral CBD 50 mg twice a day.

A clinical improvement was documented in 6 out of 8 patients with skin involvement, 2 out of 3 with lung involvement, 3 out 4 with liver involvement and 3 out of 3 with oral involvement.

The results obtained clearly indicate that administration of CBD reduces the severity of chronic GVHD.

The invention claimed is:

1. A method of preventing, ameliorating or treating graft-versus-host disease (GVHD), comprising the step of administering to a patient undergoing transplantation, either within 14 days prior to transplantation or beginning 1 to 30 days after transplantation, an effective amount of a composition lacking psychotropic effects comprising cannabidiol in doses of cannabidiol between about 5 mg to about 600 mg each administration, once to three times daily.

2. The method according to claim 1 wherein said GVHD is acute GVHD.

3. The method according to claim 1 wherein said GVHD is chronic GVHD.

4. The method according to claim 1, wherein said patient is undergoing allogeneic hematopoietic stem cell transplantation.

5. The method according to claim 4, wherein said patient is undergoing allogeneic hematopoietic stem cell transplantation in which the cells are bone marrow stem cells, peripheral-blood hematopoietic stem cell grafts, cord blood units, haploidentical peripheral-blood stem cells or haploidentical bone marrow stem cells.

6. The method according to claim 1, wherein said composition lacking psychotropic effects further comprises at least one additional therapeutic agent.

7. A method of treating graft-versus-host disease (GVHD), comprising administering to a patient suffering from GVHD a therapeutically effective amount of a composition lacking psychotropic effects comprising cannabidiol in doses of cannabidiol between about 5 mg to about 600 mg each administration, once to three times daily.

8. The method according to claim 7, wherein said patient is suffering from acute GVHD.

9. The method according to claim 7, wherein said patient is suffering from chronic GVHD.

10. The method according to claim 7, wherein said composition lacking psychotropic effects further comprises at least one additional therapeutic agent.

11. The method according to claim 1, wherein said administering comprises orally administering.

12. The method according to claim 7, wherein said administering comprises orally administering.

* * * * *